United States Patent
Bott et al.

[11] Patent Number: 5,459,216
[45] Date of Patent: Oct. 17, 1995

[54] COPOLYMERIZABLE OXIME ETHERS AND COPOLYMERS CONTAINING THEM

[75] Inventors: Kaspar Bott, Mannheim; Norbert Goetz, Worms; Gerhard Bauer, Weinheim; Oral Aydin, Mannheim, all of Germany

[73] Assignee: BASF Aktiengesellschaft, Ludwigshafen, Germany

[21] Appl. No.: 338,544

[22] PCT Filed: Jun. 3, 1993

[86] PCT No.: PCT/EP93/01396

§ 371 Date: Dec. 9, 1994

§ 102(e) Date: Dec. 9, 1994

[87] PCT Pub. No.: WO93/25519

PCT Pub. Date: Dec. 23, 1993

[30] Foreign Application Priority Data

Jun. 13, 1992 [DE] Germany .......................... 42 19 385.0

[51] Int. Cl.[6] .................................................. C08F 20/34
[52] U.S. Cl. ........................................... 526/311; 564/256
[58] Field of Search ............................. 526/311; 564/256

[56] References Cited

U.S. PATENT DOCUMENTS 4,350,801  9/1982  Grasshof ................................. 526/311
4,396,738  8/1983  Powell et al. .

FOREIGN PATENT DOCUMENTS 0003516  1/1979  European Pat. Off. .
0098729  1/1984  European Pat. Off. ................ 526/311
3112117  3/1981  Germany .
3521618  6/1985  Germany .

OTHER PUBLICATIONS

P 120:299510 pp. 20–22.

Primary Examiner—Joseph L. Schofer
Assistant Examiner—N. Sarofin
Attorney, Agent, or Firm—Oblon, Spivak, McClelland, Maier & Neustadt

[57] ABSTRACT

Copolymerizable oxime ethers of the general formula

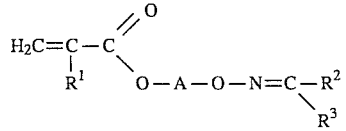

where A is a divalent link, $R^1$ may be hydrogen or $C_1$–$C_4$-alkyl and $R^2$ and $R^3$ independently of one another are each hydrogen or $C_1$–$C_{10}$-alkyl, $C_1$–$C_{10}$-alkoxy, $C_5$–$C_{10}$-cycloalkyl or $C_5$–$C_{10}$-aryl, each of which may furthermore contain 1–3 nonadjacent nitrogen, oxygen or sulfur atoms as hetero atoms in the carbon chain or in the carbon ring and may be substituted by $C_1$–$C_4$-alkyl or $C_1$–$C_4$-alkoxy groups, $R^2$ or $R^3$ may each be hydrogen or $R^2$ and $R^3$ together form a bridge of 3 to 14 carbon atoms, where some of the carbon atoms may also be part of an aromatic ring.

6 Claims, No Drawings

COPOLYMERIZABLE OXIME ETHERS AND COPOLYMERS CONTAINING THEM

The present invention relates to oxime ethers of the general formula

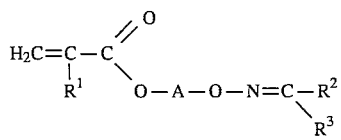

where A is a divalent link, $R^1$ may be hydrogen or $C_1$–$C_4$-alkyl and $R^2$ and $R^3$ independently of one another are each $C_1$–$C_{10}$-alkyl, $C_1$–$C_{10}$-alkoxy, $C_5$–$C_{10}$-cycloalkyl or $C_5$–$C_{10}$-aryl, each of which may furthermore contain 1–3 nonadjacent nitrogen, oxygen or sulfur atoms as hetero atoms in the carbon chain or in the carbon ring and may be substituted by from one to three $C_1$–$C_4$-alkyl or $C_1$–$C_4$-alkoxy groups, $R^2$ or $R^3$ may be hydrogen or $R^2$ and $R^3$ together form a bridge of 3 to 14 carbon atoms, where some of the carbon atoms may also be part of an aromatic ring.

Copolymers which are used in coating materials or adhesives are often crosslinkable copolymers. By means of crosslinking, for example, protective coatings or adhesive coatings having good elastic properties, high cohesion and high resistance to chemicals and to solvents can be obtained.

For crosslinking, a crosslinking agent which reacts with functional groups in the copolymer is generally added to the copolymers. Examples of possible crosslinking agents are polyisocyanates, which react with hydroxyl or amino groups.

DE-A-35 21 618 discloses corresponding aqueous adhesive formulations in which polyisocyanates dispersed in water are added, as crosslinking agents, to aqueous dispersions of copolymers obtained by free radical copolymerization. Similar coating formulations are also described in U.S. Pat. No. 43 96 738 and DE-A-31 12 117.

However, the disadvantage of these aqueous formulations is the poor shelf-life. The polyisocyanate therefore must not be dispersed in water and mixed with the copolymer until shortly before it is used as a crosslinking agent.

A longer shelf-life can be achieved by reacting the isocyanates groups with blocking agents, for example oximes, caprolactam, phenols or dialkyl maleates. The resulting blocked polyisocyanates undergo hydrolysis in aqueous dispersion only to a minor extent.

DE-A-38 07 555 relates to such a diisocyanate which is blocked with oximes, is dispersed in water and is suitable as an additive for polymers dispersed in water.

However, crosslinking reactions occur only after elimination of the blocking agent at above about 130° C.

Conventional aqueous adhesive formulations containing polyisocyanates as crosslinking agents are therefore either unstable during storage and can hence be used only as 2-component systems or undergo crosslinking only at high temperatures.

Aqueous dispersions which have a long shelf-life and crosslink at room temperature after removal of the solvent are disclosed in EP-A-3516. These dispersions contain polyhydrazides which react with carbonyl-containing monomers polymerized in the copolymer.

It is in principle desirable to develop further dispersions having a long shelf-life and crosslinking at room temperature, in order to provide alternatives to polyhydrazide crosslinking.

It is an object of the present invention to provide crosslinkable copolymers which have a long shelf-life in dispersion or solution, even in the presence of a crosslinking agent, and can be crosslinked at room temperature.

We have found that this object is achieved by the copolymerizable oxime ethers defined above and a process for their preparation.

We have also found copolymers which contain the copolymerizable oxime ethers, and the use of the copolymers as coating materials or adhesives.

The copolymers which contain the copolymerizable oxime ethers crosslink with crosslinking agents containing aldehyde or keto groups probably by the following mechanism:

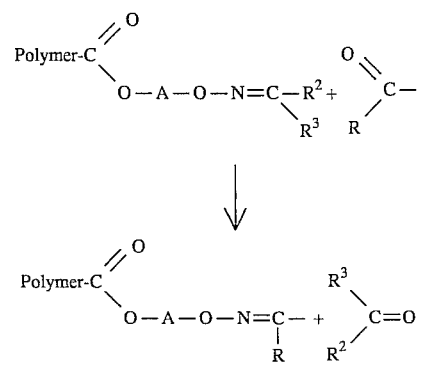

A in the general formula I is preferably a linear or branched hydrocarbon chain of 2 to 12, in particular 2 to 8, carbon atoms which may be interrupted by 1 to 3, in particular 1 or 2, nonadjacent oxygen atoms or a $C_5$–$C_{10}$-cycloalkylene or $C_5$–$C_{10}$-arylene ring. It is particularly preferably a linear or branched hydrocarbon chain of 2 to 8 carbon atoms.

$R^1$ is preferably hydrogen or methyl and $R^2$ and $R^3$ independently of one another are preferably hydrogen, $C_1$–$C_6$-alkyl, $C_1$–$C_6$-alkoxy or $C_5$–$C_{10}$-aryl, in particular a phenyl ring. In the case of the hydrogen atom only one of the two radicals $R^2$ and $R^3$ may be hydrogen.

The copolymerizable oxime ethers can be prepared, for example, by reacting an oxime ether alcohol of the formula

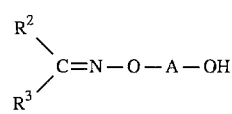

with an alkyl (meth)acrylate, in particular methyl or ethyl (meth)acrylate.

However, the reaction of an oxime ether alcohol with a (meth)acryloyl chloride or a (meth)acrylic anhydride of the formulae

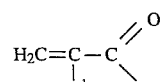

or

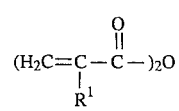

is advantageous since the reaction times can be kept short and the reaction temperatures kept low, and undesirable secondary reactions, such as polymerization and decomposition, are thus substantially avoided.

The reaction of the oxime ether alcohols II with (meth-)acryloyl chlorides III is preferably carried out with cooling of the reaction mixture at from 0° to 50° C., in particular from 10° to 30° C. In the case of the (meth)acrylic anhydrides IV, the temperature should be above 60° C. The reaction can be carried out in an organic solvent or in the absence of a solvent. Suitable solvents are, for example, cyclohexane, methylene chloride, diethyl ether, methyl tert-butyl ether and ethylene chloride.

Ethers, e.g. diethyl ether, are particularly suitable solvents also with regard to further working up. The reaction is preferably bas-catalyzed. Examples of suitable bases or basic compounds are tertiary nitrogen compounds, such as triethylamine. The base or basic compound is preferably used in equimolar amounts, based on the oxime ether alcohol.

After the end of the reaction, the reaction mixture can be washed, for example with an aqueous sodium carbonate solution, and the copolymerizable oxime ether obtained can be purified by distillation, if necessary after removal of the solvent.

The oxime ether alcohols used are obtainable by known processes, by reacting oximes with ethylene oxide or propylene oxide or with haloalcohols in the presence of a base.

The copolymerizable oxime ethers (referred to below as monomers a)) can be copolymerized with ethylenically unsaturated monomers by conventional free radical polymerization methods.

To ensure sufficient crosslinkability of the resulting copolymers, the content of polymerized oxime ethers a) should be at least 0.01% by weight. A content of more than 30% by weight is generally not necessary.

The content of polymerized oxime ethers in the copolymer is preferably from 0.1 to 10, particularly preferably from 0.1 to 5%, by weight.

The copolymers contain, as main monomers b), 30–99.99, preferably 70–99.9, particularly preferably 85–99.9%, by weight of a monomer selected from the group consisting of $C_1$–$C_{20}$-alkyl (meth)acrylates, vinyl esters of carboxylic acids of up to 20 carbon atoms, vinyl aromatics of up to 20 carbon atoms, ethylenically unsaturated nitriles, vinyl halides and nonaromatic hydrocarbons having at least 2 conjugated double bonds.

Examples of main monomers are alkyl (meth)acrylates having a $C_1$–$C_{10}$-alkyl radical, such as methyl methacrylate, methyl acrylate, n-butyl acrylate, ethyl acrylate and 2-ethylhexyl acrylate.

Mixtures of the alkyl (meth)acrylates are also particularly suitable.

Vinyl esters of carboxylic acids of 1 to 20 carbon atoms are, for example, vinyl laurate, vinyl stearate, vinyl propionate and vinyl acetate.

Suitable vinyl aromatic compounds are vinyltoluene, α- and p-styrene, α-butylstyrene, 4-n-butylstyrene, 4-n-decylstyrene and preferably styrene. Examples of nitriles are acrylonitrile and methacrylonitrile.

The vinyl halides are ethylenically unsaturated compounds substituted by chlorine, fluorine and bromine, preferably vinyl chloride and vinylidene chloride.

Examples of nonaromatic hydrocarbons having 2 to 8 carbon atoms and at least two olefinic double bonds are butadiene, isoprene and chloroprene.

The main monomers are also preferably used as a mixture.

The copolymers may furthermore contain monomers having at least one aldehyde or keto group (monomers c)).

These are preferably monomers having one or two aldehyde or keto groups or one aldehyde and one keto group or an olefinic double bond capable of undergoing free radical polymerization.

For example, acrolein, methacrolein, vinyl alkyl ketones where the alkyl radical is of 1 to 20, preferably 1 to 10, carbon atoms, formylstyrene, alkyl (meth)acrylates having one or two keto or aldehyde groups or one aldehyde and one keto group in the alkyl radical, which preferably has a total of 3 to 10 carbon atoms, for example (meth)acrylyloxyalkylpropanals, as described in DE-A-27 22 097, are suitable. N-Oxoalkyl(meth)acrylamides as disclosed in, for example, U.S. Pat. No. 4,226,007, DE-A-20 61 213 or DE-A-22 07 209 are also useful.

Acetoacetyl (meth)acrylate, acetoacetoxyethyl (meth)acrylate and in particular diacetoneacrylamide are particularly preferred.

The content of these monomers is in general from 0 to 30, in particular from 0 to 10, particularly preferably from 0 to 5%, by weight.

The copolymer may be self-crosslinkable or externally crosslinkable. In the case of self-crosslinkability, it contains both copolymerizable oxime ethers and monomers having at least one keto or aldehyde group. In this case, crosslinking of the copolymer occurs without the addition of a crosslinking agent, by reaction of the oxime group with the keto or aldehyde group in the same copolymer.

The content of the monomer having at least one keto or aldehyde group c) in the copolymer should then preferably be at least 0.1% by weight. The maximum possible amount of the main monomer is then reduced by 0.1% by weight.

Examples of further monomers d) which differ from the monomers a) to c) and may be present in the copolymer are esters of acrylic and methacrylic acid with alcohols of 1 to 20 carbon atoms which contain at least one further hetero atom in addition to the oxygen atom in the alcohol group and/or which contain an aliphatic or aromatic ring, such as 2-ethoxyethyl acrylate, 2-butoxyethyl (meth)acrylate, dimethylaminoethyl (meth)acrylate or diethylaminoethyl (meth)acrylate, aryl, alkylaryl or cycloalkyl (meth)acrylates, such as cyclohexyl (meth)acrylate, phenylethyl (meth)acrylate or phenylpropyl (meth)acrylate, or acrylates of heterocyclic alcohols, such as furfuryl (meth)acrylate.

Further monomers, such as (meth)acrylamide, and derivatives thereof which are substituted at the nitrogen by $C_1$–$C_4$-alkyl are also suitable.

Monomers having hydroxyl functions, for example $C_1$–$C_{15}$-alkyl (meth)acrylates which are substituted by one or two hydroxyl groups, are also of importance. Particularly important comonomers having hydroxyl functions are $C_1$–$C_8$-hydroxyalkyl (meth)acrylates, such as n-hydroxyethyl, n-hydroxypropyl or n-hydroxybutyl (meth)acrylate.

The concomitant use of comonomers having salt-forming groups is preferable for the preparation of self-dispersible copolymers which are suitable, for example, for aqueous secondary dispersions. Monomers having salt-forming groups are, in particular, itaconic acid, acrylic acid and methacrylic acid.

The amount of the further comonomers in the copolymer may be from 0 to 50, preferably from 0 to 20, very particularly preferably from 0 to 10%, by weight.

The copolymer A) is prepared by free radical polymerization. Suitable polymerization methods, such as mass, solution, suspension or emulsion polymerization, are known to the skilled worker.

The copolymer is preferably prepared by solution polymerization and subsequent dispersion in water or, particularly preferably, by emulsion polymerization.

In the emulsion polymerization, comonomers can be polymerized in a conventional manner in the presence of a water-soluble initiator and of an emulsifier at, preferably, from 30° to 95° C.

Examples of suitable initiators are sodium persulfate, potassium persulfate, ammonium persulfate, tert-butylhydroperoxides, water-soluble azo compounds or redox initiators.

The emulsifiers used are, for example, alkali metal salts of relatively long-chain fatty acids, alkyl-sulfates, alkylsulfonates, alkylated arylsulfonates or alkylated biphenyl ether sulfonates. Other suitable emulsifiers are reaction products of alkylene oxides, in particular ethylene oxide or propylene oxide, with fatty alcohols, fatty acids or phenols, or alkylphenols.

In the case of aqueous secondary dispersions, the copolymer is first prepared by solution polymerization in an organic solvent and is then dispersed in water without the use of an emulsifier or dispersant, with the addition of salt formers, for example of ammonia, to copolymers containing carboxylic acid groups. The organic solvent can be distilled off. The preparation of aqueous secondary dispersions is known to the skilled worker and is described in, for example, DE-A-37 20 860.

For adjusting the molecular weight, regulators may be used in the polymerization. For example, —SH-containing compounds, such as mercaptoethanol, mercaptopropanol, thiophenol, thioglycerol, ethyl thioglycolate, methyl thioglycolate and tert-dodecyl mercaptan, are suitable.

The type and amount of the comonomers is advantageously chosen so that the resulting copolymer has a glass transition temperature of, preferably, from −60° to +140° C., particularly preferably from −30° to +80° C., very particularly preferably, especially in the case of use as an adhesive, from −30° to +20° C. The glass transition temperature of the copolymer can be determined by a conventional method, such as differential thermal analysis or differential scanning calorimetry (cf. for example ASTM 3418/82, midpoint temperature).

Where the copolymer is not self-crosslinking, and therefore contains no monomers c), it is suitable to add a crosslinking agent to the copolymer to effect cross-linking. The crosslinking agent is usually a compound which contains at least two keto or aldehyde groups or at least one keto and one aldehyde group.

Examples of suitable crosslinking agents are in particular free radical copolymers (also referred to below as polymeric crosslinking agents), which contain abovementioned monomers c) as polymerized units.

For example, polymerized crosslinking agents which consist of 30–99.9, preferably 70–99.9%, by weight of the monomers b), 0.1–30, preferably 0.1–10%, by weight of the monomers c) and 0–50, preferably 0–20%, by weight of the monomers d) are suitable. The statements made above about the above copolymers are preferably applicable to the type of monomers, the glass transition temperature and the preparation.

The crosslinking agent, if required, is preferably added to the solution or dispersion of the copolymers.

However, it is also possible to combine the copolymer and the crosslinking agent only during use, for example during the coating of surfaces. For this purpose, for example, the crosslinking agent could first be applied to the surface as a primer and thereafter coating carried out with the dispersion or solution of the copolymers.

The solution or dispersion of the novel copolymers is suitable, for example, for use as a coating material for various substrates having plastic, wood or metal surfaces or, for example, for textiles, nonwovens, leather or paper. It is also suitable for applications in building chemistry, for example as adhesives, sealing compounds, binders or the like.

The dispersions or solutions may also contain conventional assistants or additives, depending on the intended use. These include, for example, fillers, such as quartz powder, quartz sand, finely divided silica, barite, calcium carbonate, chalk, dolomite or talc, which are often used together with suitable wetting agents, for example polyphosphates, such as sodium hexametaphosphate, naphthalenesulfonic acid or ammonium or sodium polyacrylates, the wetting agents being added in general in an amount of from 0.2 to 0.6% by weight, based on the fillers.

Fungicides for preservation may also be added. These are used in general in amounts of from 0.02 to 1% by weight, based on the dispersions or solutions. Examples of suitable fungicides are phenol or cresol derivatives or organotin compounds.

The dispersions or solutions are also particularly suitable as sealant or adhesive formulations, in particular as laminating adhesives for the production of laminated films and high-gloss films. As such, they may contain, in addition to the abovementioned additives, special assistants and additives conventionally used in adhesives technology. These include, for example, thickeners, plasticizers or tackifiers, for example natural resins or modified resins, such as rosin esters, or synthetic resins, such as phthalate resins.

The dispersions or solutions of self-crosslinking copolymers or externally crosslinking copolymers which also contain a crosslinking agent have a long shelf-life. Crosslinking occurs at as low as room temperature with volatilization of the solvent.

The coatings or adhesive bonds produced using these dispersions or solutions have good resistance to chemicals or solvents and good internal strength (cohesion).

EXAMPLES

Preparation of the copolymerizable oxime ethers

EXAMPLE 1

Apparatus: 1 l stirred glass flask with reflux condenser, dropping funnel and $CaCl_2$ tube.

A solution of 47.1 g (0.52 mol) of acryloyl chloride in 100 ml of diethyl ether was added dropwise to a mixture of 400 ml of diethyl ether, 58.5 g (0.50 mol) of O-(2-hydroxyethyl)-acetone oxime and 53.0 g (0.52 mol) of triethylamine, with stirring. The temperature of the reaction mixture was kept at 20°–22° C. by cooling with ice water. Stirring was then carried out for a further 4 hours at 25° C.

1 l of 5% strength sodiumcarbonate solution were then added to the contents of the flask and stirring was continued for 20 minutes. Thereafter, the (upper) ether phase was separated off and evaporated down at 20 mbar and 25° C., and the evaporation residue was distilled under reduced pressure without a distillation column (cf. Table 1).

This gave 74 g (87% yield) of pure acetone oxime 2-acryloyloxyethyl ether, which was identified from its H-NMR spectrum in $D_6$-DMSO: δ=1.75 (s, 3H, $CH_3$); 1.79 (s, 3H, $CH_3$); 4.15 (t, 2H, —$CH_2$—); 4.30 (t, 2H, —$CH_2$—); 5.95 (d, 1H, (β)=CH—); 6.20 (dd, 1H, (α)=CH—) and 6.35 (d, 1H, (β)=CH—).

EXAMPLE 2

209.4 g (1.36 mol) of methacrylic anhydride were added dropwise in the course of 45 minutes to a mixture of 152 g (1.30 mol) of O-(2-hydroxyethyl)-acetone oxime, 131.3 g (1.30 mol) of triethylamine and 0.40 g of phenothiazine (stabilizer) at 60° C., and the reaction was allowed to continue for a further 45 minutes. The contents of the flask were cooled to room temperature and shaken with a solution of 179.4 g (1.30 mol) of potassium carbonate in 1 l of water. The upper phase was separated off in a separating funnel and distilled under reduced pressure without a distillation column. 209 g (87% yield) of pure acetone oxime 2-methacryloyloxyethyl ether were obtained.

Elemental analysis: Calculated C 58.36 H 8.16 O 25.91
Found C 58.0 H 8.2 O 25.8

EXAMPLES 3 TO 11

The preparation of the further oxime ethers was carried out similarly to Example 1 or 2 (cf. Table 1).

TABLE 1

Preparation of the polymerizable oxime ethers

| Example | Polymerizable oxime ethers | Starting materials (solvent) |
|---|---|---|
| 1 | $(H_3C)_2C=N-O-(CH_2)_2-O-C(=O)-CH=CH_2$ | $(H_3C)_2C=N-O-(CH_2)_2-OH$; $CH_2=CH-C(=O)Cl$; $N(C_2H_5)_3$ (Diethyl ether) |
| 2 | $(H_3C)_2C=N-O-(CH_2)_2-O-C(=O)-C(CH_3)=CH_2$ | $(H_3C)_2C=N-O-(CH_2)_2-OH$; $(CH_2=C(CH_3)-C(=O)-)_2O$; $N(C_2H_5)_3$ (no solvent) |
| 3 | $(H_3C)_2C=N-O-CH_2-CH(CH_3)-O-C(=O)-C(CH_3)=CH_2$ | $(H_3C)_2C=N-O-CH_2-CH(CH_3)-OH$; $(CH_2=C(CH_3)-C(=O)-)_2O$; $N(C_2H_5)_3$ |
| 4 | $(H_3C)_3C(H)C=N-O-(CH_2)_2-O-C(=O)-C(CH_3)=CH_2$ | $(H_3C)_3C(H)C=N-O-(CH_2)_2-OH$; $CH_2=C(CH_3)-C(=O)Cl$; $N(C_2H_5)_3$ (Diethyl ether) |
| 5 | $(H_3C)_2C=N-O-(CH_2)_3-O-C(=O)-CH=CH_2$ | $CH_2=CH-C(=O)Cl$; $(H_3C)_2C=N-O-(CH_2)_3-OH$; $N(C_2H_5)_3$ (Diethyl ether) |

TABLE 1-continued

Preparation of the polymerizable oxime ethers

| Example | Polymerizable oxime ethers | Starting materials (solvent) |
|---|---|---|
| 6 | $\underset{H_3C}{\overset{H_3C}{>}}C=N-O-(CH_2)_3-O-\overset{O}{\overset{\|}{C}}-\overset{CH_3}{\overset{\|}{C}}=CH_2$ | $\left(\underset{CH_2=C-C}{\overset{CH_3}{\|}}\overset{\nearrow O}{\underset{\diagdown}{}}\right)_2 O$<br>$N(C_2H_5)_3$<br>$\underset{H_3C}{\overset{H_3C}{>}}C=N-O-(CH_2)_3-OH$ |
| 7 | $\underset{H_3C}{\overset{H_3C}{>}}C=N-O-(CH_2)_6-O-\overset{O}{\overset{\|}{C}}-\overset{CH_3}{\overset{\|}{C}}=CH_2$ | $\left(\underset{CH_2=C-C}{\overset{CH_3}{\|}}\overset{\nearrow O}{\underset{\diagdown}{}}\right)_2 O$<br>$\underset{H_3C}{\overset{H_3C}{>}}C=N-O-(CH_2)_6-OH$<br>$N(C_2H_5)_3$ |
| 8 | $Ph-\overset{CH_3}{\underset{\|}{C}}=N-O-(CH_2)_2-O-\overset{O}{\overset{\|}{C}}-CH=CH_2$ | $CH_2=CH-\overset{\nearrow O}{\underset{\diagdown Cl}{C}}$<br>$Ph-\overset{CH_3}{\underset{\|}{C}}=N-O-(CH_2)_2OH$<br>$N(C_2H_5)_3$  (Diethyl ether) |
| 9 | $Ph-\overset{CH_3}{\underset{\|}{C}}=N-O-(CH_2)_2-O-\overset{O}{\overset{\|}{C}}-\overset{CH_3}{\overset{\|}{C}}=CH_2$ | $\left(\underset{CH_2=C-C}{\overset{CH_3}{\|}}\overset{\nearrow O}{\underset{\diagdown}{}}\right)_2 O$<br>$Ph-\overset{CH_3}{\underset{\|}{C}}=N-O-(CH_2)_2OH$<br>$N(C_2H_5)_3$ |
| 10 | $\underset{H_5C_2O}{\overset{H_3C}{>}}C=N-O-(CH_2)_2-O-\overset{O}{\overset{\|}{C}}-\overset{CH_3}{\overset{\|}{C}}=CH_2$ | $\left(\underset{CH_2=C-C}{\overset{CH_3}{\|}}\overset{\nearrow O}{\underset{\diagdown}{}}\right)_2 O$<br>$\underset{H_5C_2O}{\overset{H_3C}{>}}C=N-O-(CH_2)_2-OH$<br>$N(C_2H_5)_3$ |
| 11 | $\underset{H_5C_2O}{\overset{H_3C}{>}}C=N-O-CH_2-\overset{CH_3}{\underset{\|}{CH}}-O-\overset{O}{\overset{\|}{C}}-\overset{CH_3}{\overset{\|}{C}}=CH_2$ | $\left(\underset{CH_2=C-C}{\overset{CH_3}{\|}}\overset{\nearrow O}{\underset{\diagdown}{}}\right)_2 O$<br>$\underset{H_5C_2O}{\overset{H_3C}{>}}C=N-O-CH_2-\overset{CH_3}{\underset{\|}{CH}}-OH$<br>$N(C_2H_5)_3$ |

TABLE 2

Boiling points of the polymerizable oxime ethers

| Example | Boiling point under reduced pressure |
|---|---|
| 1 | 48–50° C. 0.1 mbar |
| 2 | 50–52° C. 0.2 mbar |
| 3 | 48–49° C. 0.1 mbar |
| 4 | 48–50° C. 0.05 mbar |
| 5 | 61–63° C. 0.1 mbar |
| 6 | 55–57° C. 0.2 mbar |
| 7 | 84° C. 0.1 mbar |
| 8 | 97–98° C. 0.1 mbar |
| 9 | 107–111° C. 0.1 mbar |
| 10 | 65° C. 0.1 mbar |
| 11 | 62–63° C. 0.1 mbar |

Preparation of polymeric crosslinking agents which contain carbonyl groups

Crosslinking agent 1 (V1)

200 g of demineralized water, 37 g of feed 1 (see below) and 20 g of feed 2 were initially taken in a reaction vessel having a stirrer and two feed vessels (feed 1 and feed 2) and were heated to 85° C. After 15 minutes, feed 1 was added uniformly to the reaction vessel in the course of 2 hours and feed 2 was introduced uniformly into the reaction vessel in the course of 2.5 hours. After the final addition of initiator (feed 2), the dispersion was stirred for a further hour at 85° C.

Feed 1: (This feed was stirred during the polymerization)

107.5 g of demineralized water 400 g of ethyl acrylate 90 g of methyl methacrylate 50 g of a 20% strength by weight aqueous diacetoneacrylamide solution 50 g of a 20% strength by weight solution of the sodium salt of p-dodecyldiphenyl ether disulfonate in water (emulsifier)

50 g of a 20% strength by weight solution of the reaction product of p-isononylphenol with about 50 mol of ethylene oxide in water (emulsifier)

Feed 2:

100 g of demineralized water 3 g of sodium persulfate

Crosslinking agents V2 to V4 were prepared in a similar manner (Table 3).

TABLE 3

Composition of the crosslinking agents in % by weight

| Crosslinking agent | EA | MMA | HEA | DAA | AAEM |
|---|---|---|---|---|---|
| V1 | 80 | 18 | | 2 | |
| V2 | 96 | | | 4 | |
| V3 | 77.7 | 17.4 | | | 4.9 |
| V4 | 96 | | 2 | 2 | |

TABLE 3-continued

Composition of the crosslinking agents in % by weight

| Crosslinking agent | EA | MMA | HEA | DAA | AAEM |
|---|---|---|---|---|---|

EA: Ethyl acrylate
MMA: Methyl methacrylate
HEA: Hydroxyethyl acrylate
DAA: Diacetoneacrylamide
AAEM: Acetoacetoxyethyl methacrylate

Preparation of dispersions which contain externally crosslinking copolymers (D1–D4)

The preparation was carried out as described under V1, the feeds having the following composition:

Feed 1: (This feed was stirred during the polymerization)

107.5 g of demineralized water 400 g of ethyl acrylate 90 g of methyl methacrylate 5 g of an oxime ether according to Table 4 50 g of a 20% strength by weight solution of the sodium salt of p-dodecyldiphenyl ether disulfonate in water (emulsifier)

50 g of a 20% strength by weight solution of the reaction product of p-isononylphenol with about 50 mol of ethylene oxide in water (emulsifier)

Feed 2:

100 g of demineralized water 3 g of sodium persulfate

TABLE 4

Dispersions of externally crosslinking copolymers D1–D4

| Dispersion | Oxime ether (from Table 1) |
|---|---|
| D1 | 1 |
| D2 | 7 |
| D3 | 8 |
| D4 | 10 |

Preparation of dispersions which contain self-crosslinking copolymers (D5–D8)

The preparation was carried out as described under V1, the feeds having the following composition:

Feed 1: (This feed was stirred during the polymerization)

107.5 g of demineralized water 400 g of ethyl acrylate 90 g of methyl methacrylate 50 g of a 20% strength by weight aqueous diacetoneary-lamide [sic] solution 5 g of an oxime ether according to Table 5

50 g 50 g [sic] of a 20% strength by weight solution of the sodium salt of p-dodecyldiphenyl ether disulfonate in water (emulsifier)

50 g of a 20% strength by weight solution of the reaction product of p-isononylphenol with about 50 mol of ethylene oxide in water (emulsifier)

Feed 2:

100 g of demineralized water 3 g of sodium persulfate

TABLE 5

| Dispersion | Oxime ether (from Table 1) |
|---|---|
| D5 | 1 |
| D6 | 7 |
| D7 | 8 |
| D8 | 10 |

Testing of the dispersions for crosslinkability and performance characteristics

Crosslinkability (test based on swelling behavior)

The resulting dispersions of the crosslinking agents V1–V4 were each mixed with the externally cross-linking dispersions D1–D4 in a weight ratio of 1:1 (Table 4).

200 g of each of the resulting mixtures or 200 g of the self-crosslinking dispersions D5–D8 were converted into films, and the films were dried for 1 week at room temperature. The swelling behavior was then investigated as a measure of the degree of crosslinking of these films in tetrahydrofuran by storing about 1 g of the films of the samples in tetrahydrofuran for 2 days and measuring the solvent absorption in % (results in Table 6).

In the case of crosslinked polymers, swelling occurs through absorption of solvent. This swelling decreases with an increasing degree of crosslinking since less solvent can be absorbed by the closely crosslinked polymer. Polymers which exhibit little or no crosslinking are dissolved to a considerable extent by solvents or swell excessively when a small number of crosslinking points are present.

Production of laminated films and testing of the peel strength

The above mixtures and dispersions D5 to D8 were applied by means of a knife coater to various films heated to 50° C. (polyethylene terephthalate: PETP, polyamide: PA, polyvinyl chloride: PVC) to give a dry film thickness of 3 g/m$^2$ and were laminated with a corona-pretreated polyethylene film (PE). The films were then stored for 7 days at room temperature and under standard humidity conditions, after which they were slit into 2 cm wide strips. These strips were then peeled off at 23° C. at an angle of 180° C. [sic] at a speed of 100 m/min. The peeling force in N was determined for the 2 cm wide strips (Table 6).

TABLE 6

Solvent absorption and peel strength

| Dispersion | Crosslinking agent | Solvent absorption % | Peel strengths of the laminated films in N/cm | | |
|---|---|---|---|---|---|
| | | | PETP/PE | PA/PE | PVC/PE |
| D1 | V1 | 1400 | 3.8 | 2.4 | 5.0 |
| D2 | V1 | 1200 | 4.1 | 2.3 | 4.8 |
| D3 | V1 | 1410 | 3.9 | 2.7 | 5.2 |
| D4 | V1 | 1430 | 4.0 | 2.6 | 5.1 |
| D1 | V2 | 1130 | 3.8 | 2.7 | 4.2 |
| D2 | V2 | 1010 | 3.5 | 3.0 | 4.9 |
| D3 | V2 | 1090 | 4.0 | 3.1 | 5.2 |
| D4 | V2 | 1100 | 3.9 | 2.8 | 4.8 |
| D1 | V3 | 1200 | 4.2 | 2.3 | 5.0 |
| D2 | V3 | 1090 | 3.8 | 2.4 | 4.7 |
| D3 | V3 | 1280 | 3.7 | 2.2 | 4.6 |
| D4 | V3 | 1260 | 3.5 | 2.6 | 4.8 |
| D1 | V4 | 1500 | 3.9 | 2.6 | 5.0 |
| D2 | V4 | 1380 | 3.8 | 2.5 | 4.7 |
| D3 | V4 | 1450 | 4.0 | 3.0 | 4.6 |
| D4 | V4 | 1500 | 3.7 | 2.8 | 4.9 |
| D5 | — | 1380 | 4.0 | 2.6 | 4.8 |
| D6 | — | 1190 | 4.2 | 2.5 | 4.9 |
| D7 | — | 1400 | 3.9 | 2.4 | 5.0 |
| D8 | — | 1420 | 4.1 | 2.3 | 4.6 |
| For comparison | | | | | |
| — | V1 | —* | 0.4 | 0.1 | 0.5 |
| — | V2 | —* | 0.5 | 0.1 | 0.6 |
| — | V3 | —* | 0.5 | 0.3 | 0.4 |
| — | V4 | —* | 0.5 | 0.2 | 0.4 |
| D1 | — | —* | 0.4 | 0.2 | 0.5 |
| D2 | — | —* | 0.5 | 0.1 | 0.3 |
| D3 | — | —* | 0.5 | 0.3 | 0.4 |
| D4 | — | —* | 0.5 | 0.2 | 0.4 |

*Polymers substantially dissolved

We claim:

1. A copolymerizable oxime ether of the formula

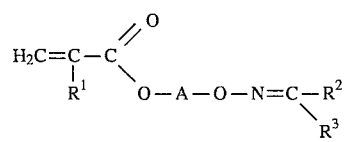

I where A is a divalent link, $R^1$ may be hydrogen or $C_1$–$C_4$-alkyl and $R^2$ and $R^3$ independently of one another are each $C_1$–$C_{10}$-alkyl, $C_1$–$C_{10}$-alkoxy, $C_5$–$C_{10}$-cycloalkyl or $C_5$–$C_{10}$-aryl, each of which may furthermore contain 1–3 nonadjacent nitrogen, oxygen or sulfur atoms as hetero atoms in the carbon chain or in the carbon ring and may be substituted by from one to three $C_1$–$C_4$-alkyl or $C_1$–$C_4$-alkoxy groups, $R^2$ or $R^3$ may be hydrogen or $R^2$ and $R^3$ together form a bridge of 3 to 14 carbon atoms, where some of the carbon atoms may also be part of an aromatic ring.

2. A process for the preparation of a copolymerizable oxime ether as claimed in claim 1, wherein an oxime ether alcohol of the formula

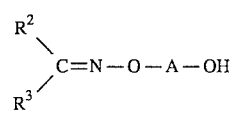

II is reacted with an acryloyl chloride of the formula

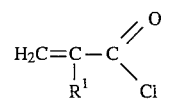

III or an acrylic anhydride of the formula

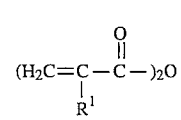

IV in the presence of a base.

3. A copolymer containing from 0.01 to 30% by weight of an oxime ether as claimed in claim 1.

4. A copolymer as claimed in claim 3, containing
 a) from 0.01 to 30% by weight of an oxime ether of the formula I,
 b) from 30 to 99.99% by weight of at least one $C_1$–$C_{20}$-alkyl (meth)acrylate, one vinyl ester of carboxylic acid of 1 to 20 carbon atoms, one vinyl aromatic of up to 20 carbon atoms, one ethylenically unsaturated nitrile of 3–6 carbon atoms, one vinyl halide or one nonaromatic hydrocarbon having 4 to 8 carbon atoms and at least 2 conjugated double bonds,
 c) from 0 to 30% by weight of at least one comonomer having at least one keto or aldehyde group and
 d) from 0 to 50% by weight of at least one further monomer,
the copolymer having a glass transition temperature of from −60° to +140° C.

5. A coating material comprising the copolymer of claim 3.

6. An adhesive comprising the copolymer of claim 3.

* * * * *